(12) United States Patent
Gleine

(10) Patent No.: US 7,430,910 B2
(45) Date of Patent: Oct. 7, 2008

(54) DEVICE FOR TESTING CABIN PARTS OF COMMERCIAL AIRCRAFTS

(75) Inventor: Wolfgang Gleine, Kakenstorf (DE)

(73) Assignee: Airbus Deutschland GmbH, Hamburg (DE)

(*) Notice: Subject to any disclaimer, the term of this patent is extended or adjusted under 35 U.S.C. 154(b) by 324 days.

(21) Appl. No.: 10/566,288

(22) PCT Filed: Dec. 20, 2004

(86) PCT No.: PCT/DE2004/002807

§ 371 (c)(1),
(2), (4) Date: Jan. 26, 2006

(87) PCT Pub. No.: WO2005/062035

PCT Pub. Date: Jul. 7, 2005

(65) Prior Publication Data
US 2006/0174706 A1  Aug. 10, 2006

(30) Foreign Application Priority Data
Dec. 23, 2003 (DE) ............... 103 61 890

(51) Int. Cl.
G01H 1/00 (2006.01)
G01N 29/12 (2006.01)

(52) U.S. Cl. ............... 73/583; 73/579

(58) Field of Classification Search ............ 73/586, 73/587, 583, 584, 579; 244/17.27, 119, 117 R
See application file for complete search history.

(56) References Cited

U.S. PATENT DOCUMENTS

| | | | |
|---|---|---|---|
| 4,181,027 A | | 1/1980 | Talbott, Jr. |
| 4,689,821 A | * | 8/1987 | Salikuddin et al. ......... 381/71.9 |
| 5,310,137 A | | 5/1994 | Yoerkie, Jr. et al. |
| 5,400,296 A | * | 3/1995 | Cushman et al. ............... 367/1 |
| 5,591,913 A | | 1/1997 | Tucker |
| 5,663,504 A | * | 9/1997 | Kluft ........................... 73/660 |
| 5,798,457 A | * | 8/1998 | Paulson ....................... 73/587 |
| 6,158,690 A | | 12/2000 | Wadey et al. |
| 6,484,580 B2 | | 11/2002 | Eagen et al. |

FOREIGN PATENT DOCUMENTS

| | | | |
|---|---|---|---|
| DE | 10361889 | * | 7/2005 |
| GB | 2 127 964 | | 4/1984 |
| JP | 06-298193 | | 10/1994 |
| WO | WO 00/28802 | | 5/2000 |

* cited by examiner

Primary Examiner—Helen C. Kwok
(74) Attorney, Agent, or Firm—W. F. Fasse; W. G. Fasse

(57) ABSTRACT

A simulation arrangement is used for laboratory testing of enclosed partial cabins to be installed as resting cabins in commercial aircraft. The partial cabin is outfitted with vibration generators for simulating the excitation of structure-borne noise corresponding to noise that will be caused by the later connection to the aircraft fuselage. Elements for exciting airborne noise are also allocated to the partial cabin. The vibration generators and the elements for the airborne noise excitation are adjustable via control and regulating devices. The signals are generated via a computer unit with an input data file of knowledge-based information and/or by extrapolation of the acoustic values at the installation location and of the details of the construction of the partial cabin.

5 Claims, 1 Drawing Sheet

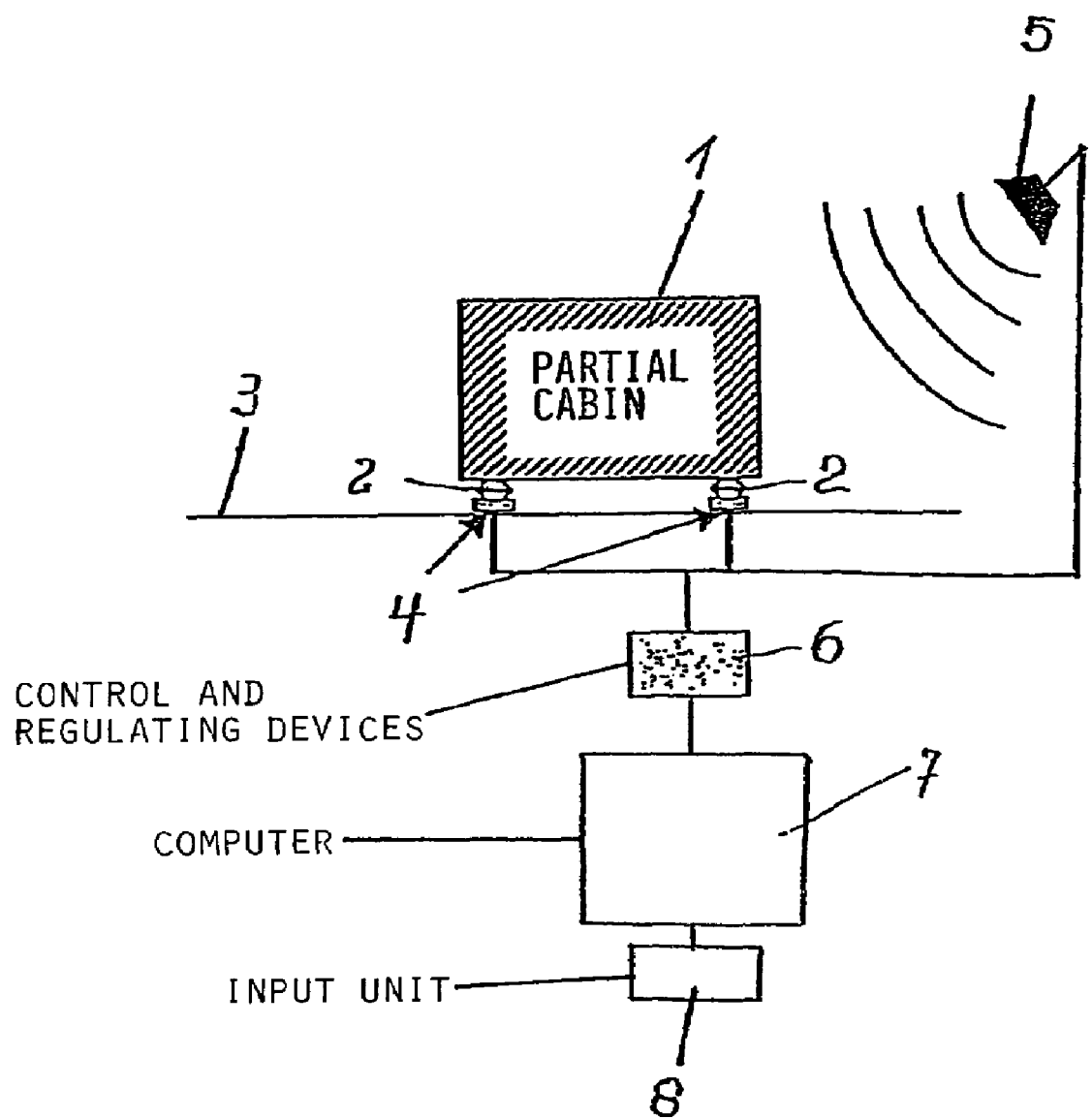

DEVICE FOR TESTING CABIN PARTS OF COMMERCIAL AIRCRAFTS

FIELD OF THE INVENTION

The invention relates to an apparatus for the laboratory testing of enclosed partial cabins as a resting room or space for installation in commercial aircraft for an acoustic design and testing.

BACKGROUND INFORMATION

The acoustic design or layout of enclosed partial cabins within cabin or freight compartment often has to satisfy especially high noise protection requirements for the purpose of the relaxation/sleep of the aircraft crew or passengers. In that regard, the installation location of the partial cabins is frequently fixed or specified in surrounding environments with especially high background or environmental noise levels. Therefore, in the acoustic design of the partial cabin, it depends on taking into account the background or environmental noise about the partial cabin and the noise transmission paths.

It is known to install the partial cabin in an original fuselage section, and to produce a diffuse noise field as an acoustic re-creation of engine jet noise and boundary layer noise outside of the section with the aid of reverberation chambers mounted or built onto the fuselage contour. Thereby, the fuselage section is excited to undergo vibrations, which, on its part, radiates noise in the form of airborne noise and also structure-borne noise inwardly toward the inside and thus also in the direction of the partial cabin, and thereby acoustically excites the partial cabin.

In that regard, the fuselage section divides the externally applied noise excitation with correct proportions into inwardly directed airborne and structure-borne noise. The structure-borne noise coupling into the partial cabin runs into the fuselage segment with correct intensity and phase due to the original partial cabin installation. Thereby, noise level measurements in the partial cabin are representative, and modifications of the partial cabin for the purpose of noise reduction measures can be designed and tested or measured.

However, this process or manner of proceeding always requires the availability of an original fuselage section, which leads to high costs especially in connection with high capacity aircraft.

SUMMARY OF THE INVENTION

It is the object of the invention, to carry out a design and testing of enclosed partial cabins outside of a fuselage section in a simple manner, and thus to make possible a laboratory handling.

The solution to this object is achieved according to the invention in that the partial cabin is arranged via at least one vibration generator for the simulation of an excitation structure-borne noise in the area of connection elements to the fuselage structure, and elements for the airborne noise excitation are allocated to the partial cabin, whereby the vibration generators for the structure-borne noise and the elements for the airborne noise excitation are adjustable via control and regulating devices, and the signals are generatable via a computer unit with an input data file of knowledge-based data as well as, if applicable, by extrapolation of the acoustic values at the installation location and of the embodiment or construction of the partial cabin.

Hereby a simple computer assisted or supported simulation of the acoustic relationships is made possible, and a plurality of changes and tests can be carried out in a simple manner, without carrying out the corresponding installations of the partial cabin in the fuselage sectors.

It is further suggested that the input data file of knowledge-based data at least the proportions of the various different noise transmissions from analyses of existing installed acoustically-designed partial cabins as well as of the measured values of the present subject relationships in the aircraft with respect to installation locations.

A simple arrangement consists in that an allocated loudspeaker arrangement is controlledly driveable or actuatable for the airborne noise excitation.

Alternatively it is suggested that reverberation chambers are arranged directly on the sidewalls of the partial cabin for the airborne noise excitation.

BRIEF DESCRIPTION OF THE DRAWING

An arrangement according to the invention is schematically illustrated in the drawing.

DETAILED DESCRIPTION OF AN EXAMPLE EMBODIMENT OF THE INVENTION

In this regard, a partial cabin 1 is set-up or erected outside of the aircraft fuselage on the floor 3 of a testing hall via the typically utilized shock absorbers 2.

Piezo vibration generators 4 for the generation of the excitation structure-borne noise are arranged below the shock absorbers 2. In this case, a loudspeaker arrangement 5 is allocated to the partial cabin 1 for the airborne noise excitation.

The elements 4, 5 for the structure-born noise and airborne noise excitation are adjusted via control and regulating devices 6, and are supplied via a computer unit 7.

In that regard, the computer unit 7 is fed or supplied with an input unit 8, which comprises knowledge-based data, and in this regard at least the proportions of the various different noise transmissions from analyses of existing installed acoustically-designed partial cabins 1. Additionally, measured values of the present subject relationships in the aircraft with respect to the installation location are taken into account.

Through these measures, the correct relationships between excitation airborne noise and excitation structure-borne noise are set in an adjusted manner, as also for the structure-borne noise excitation, to adjust the vibration components and phases corresponding per excitation point, essentially at low frequencies, at the vibration generators 4.

The informations for the individual portions or components of the noise transmission are obtained from analyses of partial cabins that are already acoustically designed and that are installed in an original fuselage section. Through additional measurements in the aircraft as well as an extrapolation of the acoustic relationships on the new design or layout situation, such as a different fuselage, different partial cabin, is taken into consideration with the aid of acoustic simulation and calculation or computation methods (SEA, FEM).

The invention claimed is:

1. Apparatus for carrying out a laboratory testing of an enclosed partial cabin to be installed as a resting cabin in a commercial aircraft, for an acoustic design and testing, characterized in that the partial cabin (1) is arranged via at least one vibration generator (4) for the simulation of an excitation structure-borne noise in an area of connection elements (2) to be connected to a fuselage structure of the aircraft, and elements (5) for an airborne noise excitation are allocated to the partial cabin (1), whereby the at least one vibration generator (4) for the structure-borne noise and the elements (5) for the airborne noise excitation are adjustable via control and regulating devices (6), based on signals that are generatable via a computer unit (7) with an input data file (8) of knowledge-based data, as well as, if applicable, by extrapolation of acoustic values at an installation location of the partial cabin in the commercial aircraft and of the design of the partial cabin (1).

2. Apparatus according to claim 1, characterized in that the input data file (8) of knowledge-based data contains at least components of various different noise transmissions from analyses of existing installed acoustically-designed partial cabins (1) as well as of measured noise values in the aircraft with respect to installation locations.

3. Apparatus according to claim 1, characterized in that the at least one vibration generator (4) of the partial cabin (1) is respectively embodied as a piezo vibration generator.

4. Apparatus according to claim 1, characterized in that the elements for the airborne noise excitation comprise an allocated loudspeaker arrangement (5) that is controlledly driveable or actuatable.

5. Apparatus according to claim 1, characterized in that the elements for the airborne noise excitation comprise reverberation chambers arranged directly on sidewalls of the partial cabin (1).

* * * * *

UNITED STATES PATENT AND TRADEMARK OFFICE
CERTIFICATE OF CORRECTION

PATENT NO.         : 7,430,910 B2
APPLICATION NO.    : 10/566288
DATED              : October 7, 2008
INVENTOR(S)        : Wolfgang Gleine Page 1 of 1

It is certified that error appears in the above-identified patent and that said Letters Patent is hereby corrected as shown below:

Column 2,
Line 4, after "data", insert --includes--;
      after "at least the", replace "proportions" by --portions or components--.

Signed and Sealed this

First Day of December, 2009

David J. Kappos
*Director of the United States Patent and Trademark Office*